United States Patent [19]
LeMahieu et al.

[11] Patent Number: 5,904,672
[45] Date of Patent: May 18, 1999

[54] ABSORBENT ARTICLE HAVING IMPROVED WAIST REGION DRYNESS AND METHOD OF MANUFACTURE

[75] Inventors: Lynn Kirkpatrick LeMahieu, Hortonville; Marianne Keevil Leick, Appleton, both of Wis.

[73] Assignee: Kimberly-Clark Worldwide, Inc., Neenah, Wis.

[21] Appl. No.: 08/515,505

[22] Filed: Aug. 15, 1995

[51] Int. Cl.⁶ .............................. A61F 13/15; A61F 13/20
[52] U.S. Cl. ....................... 604/378; 604/385.1; 428/297; 428/304.4
[58] Field of Search ..................... 604/358, 368, 604/378, 381, 385.1, 385.2; 428/297, 304.4

[56] References Cited

U.S. PATENT DOCUMENTS

| | | | |
|---|---|---|---|
| 560,289 | 5/1896 | Warner | 2/53 |
| 3,237,625 | 3/1966 | Johnson | 128/288 |
| 3,368,563 | 2/1968 | Scheier | 128/288 |
| 3,612,055 | 10/1971 | Mesek et al. | 128/287 |
| 3,825,006 | 7/1974 | Ralph | 128/287 |
| 3,828,785 | 8/1974 | Gamm et al. | 128/288 |
| 4,173,046 | 11/1979 | Gallagher | 5/484 |
| 4,315,508 | 2/1982 | Bolick | 604/392 |
| 4,388,075 | 6/1983 | Mesek et al. | 604/385 |
| 4,500,316 | 2/1985 | Damico | 604/389 |
| 4,699,823 | 10/1987 | Kellenberger et al. | 428/219 |
| 4,798,603 | 1/1989 | Meyer et al. | 604/378 |
| 4,847,134 | 7/1989 | Fahrenkrug et al. | 428/138 |
| 4,861,652 | 8/1989 | Lippert et al. | 428/284 |
| 4,886,512 | 12/1989 | Damico et al. | 609/385.2 |
| 4,904,249 | 2/1990 | Miller et al. | 604/378 |
| 4,916,005 | 4/1990 | Lippert et al. | 428/192 |
| 4,938,754 | 7/1990 | Mesek | 604/385.2 |
| 5,032,121 | 7/1991 | Mokry | 604/385.2 |
| 5,147,343 | 9/1992 | Kellenberger | 604/368 |
| 5,192,606 | 3/1993 | Proxmire et al. | 428/284 |
| 5,227,107 | 7/1993 | Dickenson et al. | 264/113 |
| 5,263,948 | 11/1993 | Karami et al. | 604/383 |
| 5,297,296 | 3/1994 | Moretz et al. | 2/237 |
| 5,304,162 | 4/1994 | Kuen | 604/391 |
| 5,324,277 | 6/1994 | Daugan et al. | 604/369 |
| 5,364,382 | 11/1994 | Latimer et al. | 604/378 |
| 5,374,262 | 12/1994 | Keuhn, Jr. et al. | 604/391 |
| 5,386,595 | 2/1995 | Kuen et al. | 2/400 |
| 5,411,498 | 5/1995 | Fahrenkrug et al. | 604/385.2 |

FOREIGN PATENT DOCUMENTS

| | | |
|---|---|---|
| 1316804 | 4/1993 | Canada . |
| 0269401 | 6/1988 | European Pat. Off. . |

*Primary Examiner*—John G. Weiss
*Assistant Examiner*—Ki Yong O
*Attorney, Agent, or Firm*—Patricia A. Charlier; Thomas M. Gage

[57] ABSTRACT

An absorbent article includes a generally reduced length absorbent assembly positioned between a moisture barrier and a bodyside liner. The moisture barrier and the bodyside liner extend beyond the absorbent assembly and define at least one waist region with a length dimension greater than about 10 centimeters. A moisture control layer is present in from about 25 to 100 percent of the area of the first waist region. The moisture control layer is configured to accommodate liquid that may be present in the waist region as a result of condensation or perspiration and also limit the transport of liquid from the absorbent assembly into the waist region.

13 Claims, 4 Drawing Sheets

ABSORBENT ARTICLE HAVING IMPROVED WAIST REGION DRYNESS AND METHOD OF MANUFACTURE

BACKGROUND OF THE INVENTION

Many absorbent articles such as incontinence garments, diapers and training pants have a generally centralized crotch region housing an absorbent structure. The absorbent structure is adapted to take in and retain body excretions. Toward the longitudinal ends, these absorbent articles include regions which are commonly referred to as end-seal regions or waistband regions. When the absorbent article is worn, the end-seal regions are positioned against the abdomen and lower back of the wearer. The end-seal regions commonly include elastic members to form physical leakage barriers and fastening components to secure the absorbent article about the wearer.

An important factor in the design of absorbent articles is the dryness and comfort of the wearer. Much of the attention paid to maintaining the dryness of the absorbent article has focused on improving the absorbent structure. In fact, absorbent technology advances have increased the efficiency of absorbent structures to the point where they can be much thinner and smaller than previously possible. In some products, however, particularly those such as disposable undergarments that include fastening components in the end-seal regions, the ability to decrease the length of an absorbent structure does not necessarily translate into a reduction in the overall length of the product. Instead, the decrease in the length of the absorbent structure may only lead to an increase in the length of the end-seal regions.

Simply as a consequence of their size, larger end-seal regions, referred to herein as waist regions, play a greater role in determining the dryness and comfort of the wearer. Unfortunately, existing products have employed materials which tend to wick liquid from the absorbent structure into the waist regions. As can well be imagined, once distributed into the waist regions this liquid can create a damp, uncomfortable sensation. Furthermore, some liquid capacity is needed in the waist regions to acquire perspiration and condensation that may form in the waist regions and isolate the perspiration and condensation from the skin of the wearer. When the materials used in the waist regions transport liquid into the waist regions from the crotch region, the liquid capacity of the waist regions is depleted or exhausted and thus not available for perspiration and condensation.

Therefore, what is lacking and needed in the art is an absorbent article having a relatively large waist region that can accommodate condensation and perspiration within the waist region without separately transporting liquids from the absorbent structure into the waist region.

SUMMARY OF THE INVENTION

In response to the discussed deficiencies of the prior art, a new absorbent article has been developed. The absorbent article has an absorbent structure with a relatively small length dimension in relation to the overall length of the article, yet keeps the wearer dry in the waist regions by incorporating a moisture control layer that is adapted to accommodate condensation and perspiration without transporting liquid from the absorbent structure into the waist regions.

In one aspect, the present invention concerns an absorbent article having a longitudinal axis and a moisture barrier including a liquid impermeable material. The moisture barrier has a first end edge and a second end edge longitudinally separated from the first end edge. An absorbent assembly of the absorbent article has opposite longitudinal ends, and the absorbent assembly is disposed on the moisture barrier between its first and second end edges. A liquid permeable bodyside liner of the absorbent assembly is bonded to the moisture barrier with the absorbent assembly disposed between the bodyside liner and the moisture barrier. The moisture barrier and the bodyside liner extend beyond the longitudinal ends of the absorbent assembly and thereby define first and second waist regions. The waist regions represent those portions of the absorbent article between the longitudinal ends of the absorbent assembly and the respective first and second end edges of the moisture barrier. The first waist region has a width dimension, a length dimension parallel to the longitudinal axis and greater than about 10 centimeters, and an area. The absorbent article also includes a moisture control layer having a liquid wicking rate less than about 3 centimeters per one half hour and a total water capacity of at least about 0.5 gram. The moisture control layer is present in from about 25 to 100 percent of the area of the first waist region.

This aspect of the invention concerns an absorbent article with a waist region that represents a substantial portion of the overall length of the absorbent article. The moisture control layer is present in a substantial portion of the waist region, and may additionally be present in both waist regions. The moisture control layer is adapted to have a liquid wicking rate that reduces or even eliminates the transport of liquid from the absorbent assembly into the waist region under normal use conditions. Further, the moisture control layer is adapted to have a liquid capacity of sufficient magnitude to accommodate the quantity of liquid that could be expected in this larger waist region due to condensation and perspiration.

In another aspect, the invention pertains to a method of making an absorbent article. The method includes the steps of: providing a moisture barrier comprising a liquid impermeable material, the moisture barrier having a first end edge and an opposite second end edge longitudinally spaced from the first end edge; disposing an absorbent assembly on the moisture barrier between the first and second end edges, the absorbent assembly having opposite longitudinal ends; disposing a liquid permeable bodyside liner on the moisture barrier with the absorbent assembly disposed therebetween, the moisture barrier and the bodyside liner extending beyond the longitudinal ends of the absorbent assembly and defining first and second waist regions between the longitudinal ends and the respective first and second end edges, the first waist region having a width dimension, a length dimension parallel to the longitudinal axis and greater than about 10 centimeters, and an area; providing a moisture control layer having a liquid wicking rate of less than about 3 centimeters per 30 minutes and a total water capacity of at least about 0.5 gram; positioning the moisture control layer in the first waist region with the moisture control layer present in from about 25 to 100 percent of the area of the first waist; and bonding the moisture barrier, the bodyside liner and the moisture control layer together.

In still another aspect, the invention pertains to a method of making an absorbent article including the steps of: providing a first continuous web comprising a liquid impermeable moisture barrier; disposing a plurality of absorbent assemblies on the first continuous web at spaced locations; providing a plurality of sheets of a moisture control material, the moisture control material having a total water capacity of from about 1 to about 15 grams; disposing the sheets of moisture control material on the first continuous web between neighboring absorbent; providing a second continuous web comprising a liquid permeable bodyside liner; bonding the first continuous web, the second continuous web and the sheets of moisture control material together, with the absorbent assemblies disposed between the first and second continuous webs; and transversely cutting the first continuous web, the second continuous web and the sheets of moisture control material at locations between the neighboring absorbent assemblies to form a plurality of individual composite structures, each composite structure comprising an absorbent assembly disposed between a bodyside liner and a moisture barrier, the moisture barrier and the bodyside liner extending beyond longitudinal ends of the absorbent assembly and defining first and second waist regions between the longitudinal ends and respective first and second end edges of the moisture barrier, the first waist region having a width dimension, a length dimension parallel to the longitudinal axis and greater than about 10 centimeters, and an area, the moisture control material being present in from about 25 to 100 percent of the area of the first waist region.

Numerous features and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

DEFINITIONS

Figure 1:
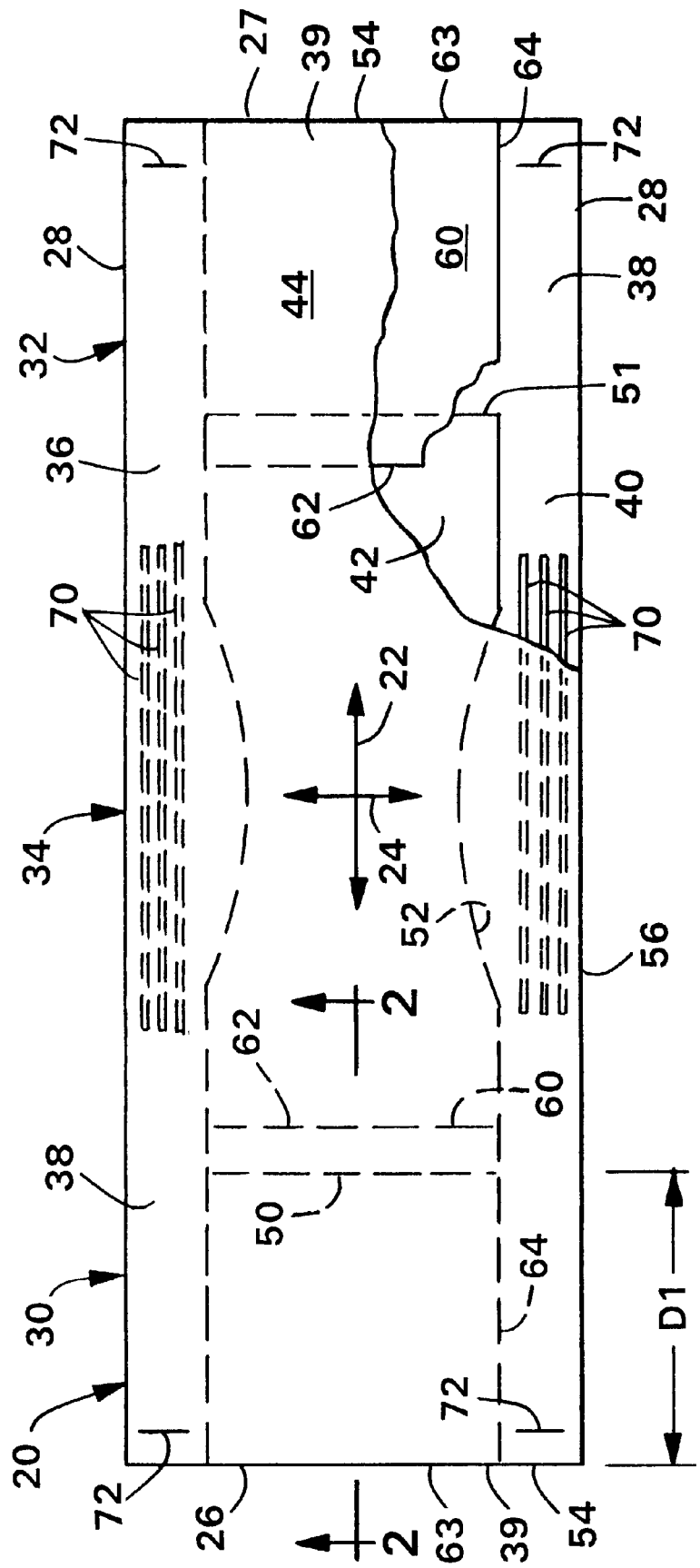
FIG. 1 representatively shows a plan view of a disposable absorbent article according to the present invention, taken from the inner garment side of the absorbent article in a stretched and laid flat condition and with portions broken away for purposes of illustration.

Within the context of this specification, each term or phrase below will include the following meaning or meanings:

(a) "Bonded" refers to the joining, adhering, connecting, attaching, or the like, of two elements. Two elements will be considered to be bonded together when they are bonded directly to one another or indirectly to one another, such as when each is directly bonded to intermediate elements.

(b) "Disposable" includes being disposed of after use and not intended to be washed and reused.

(c) "Disposed," "disposed on," "disposed with," "disposed at," "disposed near" and variations thereof are intended to mean that one element can be integral with another element, or that one element can be a separate structure bonded to or placed with or placed near another element.

(d) "Elastic," "elasticized" and "elasticity" mean that property of a material by virtue of which it tends to recover its original size and shape after removal of a force causing a deformation.

(e) "Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 200 percent, of its relaxed length and recover, upon release of an applied force, at least 50 percent of its elongation.

(e) "Extension," "extend" and "extended" mean the change in length of a material due to stretching, expressed in units of length.

(g) "Fabrics" is used to refer to all of the woven, knitted and nonwoven fibrous webs.

(h) "Finish" refers to a substance or mixture of substances added to textile materials to impart desired properties.

(i) "Flexible" refers to materials which are compliant and which will readily conform to the general shape and contours of the wearer's body.

(j) "Force" includes a physical influence exerted by one body on another which produces acceleration of bodies that are free to move and deformation of bodies that are not free to move.

(k) "Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

(l) "Integral" is used to refer to various portions of a single unitary element rather than separate structures bonded to or placed with or placed near one another.

(m) "Inward" and "outward" refer to positions relative to the center of an absorbent garment, and particularly transversely and/or longitudinally closer to or away from the longitudinal and transverse center of the absorbent garment.

(n) "Layer" when used in the singular can have the dual meaning of a single element or a plurality of elements.

(o) "Liquid impermeable" when used to describe a layer or laminate means that liquid such as urine will not pass through the layer or laminate under ordinary use conditions in a direction generally perpendicular to the plane of the layer or laminate at the point of liquid contact.

(p) "Member" when used in the singular can have the dual meaning of a single element or a plurality of elements.

(q) "Nonwoven web" means a web of material which is formed without the aid of a textile weaving or knitting process.

(r) "Operatively joined" and "operatively connected," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

(s) "Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 200 percent, of its relaxed length when it is bonded to the other member.

(t) "Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

These terms may be defined with additional language in the remaining portion of the specification.

DETAILED DESCRIPTION OF THE PREFERRED EMBODIMENTS

Figure 2:
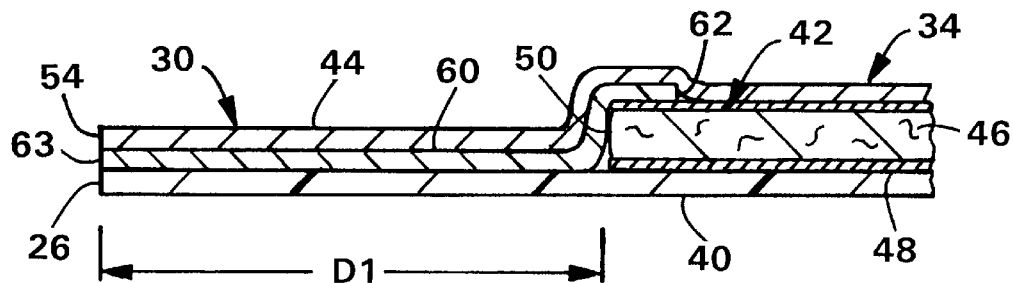
FIG. 2 representatively shows an enlarged section view taken generally from the plane of the line 2—2 in FIG. 1.

With reference to FIGS. 1 and 2, an absorbent article formed according to the invention is shown for purposes of illustration as a disposable undergarment 20 for adult incontinence. The invention may also be embodied in other absorbent articles, such as other adult incontinence products, diapers, and training pants, reusable absorbent articles, other personal care or health care garments, or the like.

In general, the undergarment 20 includes a generally reduced length absorbent assembly 42 positioned between a moisture barrier 40 and a bodyside liner 44. The moisture barrier 40 and the bodyside liner 44 extend beyond the absorbent assembly 42 and define at least one waist region 30 or 32 with a length dimension greater than about 10 centimeters. A moisture control layer 60 is disposed in the waist region 30 or 32 and configured to accommodate liquid that may be present in the waist region 30 or 32 as a result of condensation or perspiration. The moisture control layer 60 is present in a sufficient portion of the waist region, for example from about 25 to 100 percent of the area of the waist region, to keep the wearer dry and comfortable. To further keep the wearer dry and comfortable, the moisture control layer 60 is also configured to limit the transport of liquid from the absorbent assembly 42 into the waist region 30 or 32. A detailed description of several specific embodiments of the invention as well as the manner and process for making and using it are set forth below.

The illustrated undergarment 20 defines longitudinal and transverse axes, represented by arrows 22 and 24 in FIG. 1. The undergarment 20 has opposite, first and second longitudinal end edges 26 and 27, and longitudinal side edges 28 that extend between the longitudinal end edges. The undergarment 20 includes a first waist region 30, a second waist region 32, and an intermediate, crotch region 34 positioned between and interconnecting the first and second waist regions. The outer edges of the undergarment 20 define a periphery 36 in which the longitudinally extending side margins are designated 38 and the laterally extending end margins are designated 39. The end edges 26 and 27 and side edges 28 are shown as generally straight, but optionally, may be curvilinear and contoured.

The undergarment 20 includes a substantially liquid impermeable moisture barrier 40, an absorbent assembly 42 (FIG. 2) disposed on the moisture barrier, and a substantially liquid permeable bodyside liner 44 bonded to the moisture barrier to sandwich the absorbent assembly therebetween. The moisture barrier 40 and bodyside liner 44 are desirably longer and wider than the absorbent assembly 42 so that the peripheries of the moisture barrier and bodyside liner may be bonded together using ultrasonic bonds, thermal bonds, adhesives, or other suitable means. The absorbent assembly 42 may be bonded directly to the moisture barrier 40 and/or the bodyside liner 44 using ultrasonic bonds, thermal bonds, adhesives, or other suitable means.

The moisture barrier 40 desirably comprises a material that is formed or treated to be liquid impermeable. The moisture barrier 40 may comprise a single layer of material or a laminate of two or more separate layers of material. Suitable moisture barrier materials include films, wovens, nonwovens, laminates of films, wovens, and/or nonwovens, or the like. For example, the moisture barrier 40 may comprise a thin, substantially liquid impermeable web or sheet of plastic film such as polyethylene, polypropylene, polyvinyl chloride or similar material. The moisture barrier material may be transparent or opaque and have an embossed or matte surface. One particular material for the moisture barrier 40 is a polyethylene film that has a nominal thickness of about 0.025 millimeter and a systematic matte embossed pattern, and that has been corona treated on both sides. Another suitable moisture barrier material is an adhesive or thermal laminate comprising a cast or blown film formed of polypropylene, polyethylene or the like, and a spunbond web formed of polypropylene and polyethylene medium-crimped bicomponent fibers in a 50/50 side-by-side configuration. Alternatively, the moisture barrier 40 may comprise a liquid permeable material and other suitable means (not shown), such as a liquid impermeable layer associated with the absorbent assembly 42, may be provided to impede liquid movement away from the absorbent assembly.

The moisture barrier 40 may also be gas permeable, such that gases encountered during use of the absorbent garment are able to pass through the material under ordinary use conditions, over either all or part of its surface area. The moisture barrier 40 may comprise, for example, any microporous, "breathable" material which permits gases, such as water vapor, to escape while substantially preventing liquid exudates from passing therethrough. Suitable breathable materials include a microporous polymer film or a nonwoven fabric which has been coated or otherwise treated to impart a desired level of liquid impermeability, or the like. For example, a suitable microporous film is available under the trade designation PMP-1 from Mitsui Toatsu Chemicals, Inc., a company having offices in Tokyo, Japan; or a polyolefin film available under the trade designation XKO-8044 from 3M Company of Minneapolis, Minn., USA.

The present invention is thought to be particularly effective, however, in embodiments where the moisture barrier 40 comprises a substantially vapor impermeable material. For example, the moisture barrier 40 may comprises a material having a water vapor transmission rate (WVTR) value of less than about 2,000 grams per square meter per 24 hours (gm/m²/24 hr). More particularly, the moisture barrier 40 may comprise a material having a WVTR value of less than about 400 gm/m²/24 hr. One suitable procedure for measuring the WVTR value of a material is the Water Vapor Transmission Rate Test set forth in the TEST PROCEDURES section below.

The absorbent assembly 42 comprises materials adapted to absorb and retain liquid waste. The absorbent assembly 42 may comprise various absorbent materials, such as an air-formed batt of cellulosic fibers (i.e., wood pulp fluff) or a coform material composed of a mixture of cellulosic fibers and synthetic polymer fibers. Polymer fibers may be incorporated, for example, in the manner described in U.S. Pat. No. 5,227,107 issued Jul. 13, 1993 to Dickenson et al. The absorbent assembly 42 may also include compounds to increase its absorbency, such as 0–95 weight percent of organic or inorganic high-absorbency materials, which are typically capable of absorbing at least about 15 and desirably more than 25 times their weight in water. Suitable high-absorbency materials are described in U.S. Pat. Nos. 4,699,823 issued Oct. 13, 1987 to Kellenberger et al. and 5,147,343 issued Sep. 15, 1992 to Kellenberger, which are incorporated herein by reference. High-absorbency materials are available from various commercial vendors, such as Dow Chemical Company, Hoechst Celanese Corporation, and Allied Colloids, Inc. The absorbent assembly 42 may also include tissue layers or acquisition or distribution layers to help maintain the integrity of fibrous absorbents or transport liquids.

One particular absorbent assembly 42 that has been found desirable for use in undergarments for adult incontinence comprises an absorbent batt 46 at least partially encased in layers of tissue 48 (FIG. 2). The absorbent batt 46 comprises from about 70 to about 95 weight percent wood pulp fluff, from about 5 to about 25 weight percent high-absorbency materials, and from 0 to about 5 weight percent thermoplastic polypropylene filaments. The tissue layers 48 may be absent from at least a portion of the bottom surface of the absorbent batt 46 so that the absorbent batt may be bonded directly to the moisture barrier 40 using adhesives or other suitable means. Alternatively, the tissue layers 48 may fully cover the top and/or bottom surfaces of the absorbent batt 46. In particularly desirable embodiments, the absorbent assembly 42 has a length dimension of from about 25 to about 50 centimeters and a width dimension varying between about 10 and about 20 centimeters. By way of illustration, an undergarment 20 adapted for use by incontinent adults and employing such an absorbent assembly suitably has a saturated liquid retention capacity of from about 100 to about 1500 grams. The saturated retention capacity of an undergarment can be determined according to the Saturated Retention Capacity Test as set forth in the TEST PROCEDURES section below.

In the illustrated embodiment, the moisture barrier 40 extends the full length and width of the undergarment 20 and thus defines in part the first and second end edges 26 and 27 and the side edges 28. As best shown in FIG. 1, the absorbent assembly 42 has opposite longitudinal ends 50 and 51 and opposite sides 52 that extend between the ends. The longitudinal ends 50 and 51 and the sides 52 of the absorbent assembly 42 are desirably spaced inward from the end edges 26 and 27 and side edges 28 of the undergarment 20. In the longitudinal direction, for example, the absorbent structure 42 desirably has a length of from about 35 to about 75 percent of the length of the undergarment 20. The bodyside liner 44 also includes opposite end edges 54 and opposite side edges 56 that extend between the end edges. In the illustrated embodiment, the end edges 54 and side edges 56 extend to the full length and width of the undergarment 20, although the end and side edges of the bodyside liner may alternatively terminate inward of or independently form the end edges 26 and 27 and side edges 28 of the undergarment 20.

The bodyside liner 44 is formed of a liquid permeable material so that liquid waste, and possibly semi-solid waste as well, can pass through the liner and be absorbed by the absorbent assembly 42. Suitable bodyside liners 44 may comprise a nonwoven web or sheet of wet strength tissue paper, a spunbonded, meltblown or bonded-carded web composed of synthetic polymer filaments or fibers, such as polypropylene, polyethylene, polyesters or the like, or a web of natural polymer filaments or fibers such as rayon or cotton. In addition, the bodyside liner 44 is desirably non-elastic and may be treated with a surfactant to aid in liquid transfer. In a particular embodiment of the invention, the bodyside liner 44 comprises a single layer, nonwoven, spunbond polypropylene fabric composed of about 2.8–3.2 denier fibers formed into a web having a basis weight of about 17 gsm and density of about 0.11 gm/cc. The fabric is surface treated with about 0.28 weight percent of a surfactant commercially available under the trade designation Triton X-102 from Union Carbide Chemicals and Plastics Company, Inc. of Danbury, Conn., U.S.A.

The first waist region 30 is contiguous with the first end edge 26 and extends longitudinally inward therefrom toward the transverse center line 24 of the undergarment 20. For purposes of the present invention, the longitudinal boundaries of the first waist region 30 are defined by the first end edge 26 of the undergarment 20 and first longitudinal end 50 of the absorbent assembly 42. The distance between the first end edge 26 and first longitudinal end 50 measured along the longitudinal center line 22 of the undergarment 20 defines a length dimension of the first waist region 30, which is labeled D1 in FIGS. 1 and 2. In one aspect of the present invention, the first waist region 30 has a length dimension of greater than about 7 centimeters, and particularly greater than about 10 centimeters, and more desirably greater than about 12 centimeters, for improved performance. The transverse boundaries of the first waist region 30 are defined by the opposite side edges 28 of the undergarment, which define therebetween a width dimension. In particular embodiments of the invention, the length and width dimensions of the first waist region 30 are selected such that the first waist region 30 has an area of greater than about 100 square centimeters, and more particularly greater than about 150 square centimeters for improved performance.

The second waist region 32 is contiguous with the second end edge 27 and extends longitudinally inward therefrom toward the transverse center line 24. Again for purposes of the present invention, the longitudinal boundaries of the second waist region 32 are defined by the second end edge 27 of the undergarment 20 and second longitudinal end 51 of the absorbent assembly 42. The length dimension of the second waist region 32 is desirably although not necessarily the same as the length dimension of the first waist region 30. Specifically, the second waist region may have a length dimension of greater than about 7 centimeters, and particularly greater than about 10 centimeters, and more desirably greater than about 12 centimeters, for improved performance. Like the first waist region 30, the transverse boundaries of the second waist region 32 are defined by the opposite side edges 28 of the undergarment, and the dimensions of the second waist region 32 may be selected such that the second waist region 32 has an area of greater than about 100 square centimeters, and more particularly greater than about 150 square centimeters for improved performance.

The waist regions 30 and 32 comprise those upper portions of undergarment 20 which, when worn, wholly or partially cover or encircle the waist or mid-lower torso of the wearer. At least for purposes of the present invention, the intermediate, crotch region 34 comprises that portion of undergarment 20 that contains the absorbent assembly 42. More precisely, the crotch region 34 is circumscribed in the longitudinal direction 22 by the longitudinal end edges 50 and 51 of the absorbent assembly 42 and in the transverse direction 24 by the side edges 28 of the undergarment 20. When the undergarment 20 is worn, the crotch region 34 is positioned between the legs of the wearer and covers the lower torso of the wearer. Thus, the crotch region 34 is the area where insults of urine typically occur in the undergarment or other disposable absorbent article.

The undergarment 20, which is in a stretched and laid flat condition in FIG. 2, is illustrated as having a rectangular periphery 36. Of course, the undergarment 20 may optionally be hourglass-shaped, I-shaped, T-shaped, or irregularly-shaped. The general shape of the absorbent assembly 42 may have a narrowed center portion as illustrated, or may correspond to the shape of the undergarment 20 or assume a different shape.

The undergarment 20 also comprises at least one moisture control layer 60 that contributes to the dryness and comfort of the wearer. The illustrated undergarment 20 includes two moisture control layers 60, with one present in the first waist region 30 and the other present in the second waist region 32. Each moisture control layer 60 has opposite inner and outer edges 62 and 63 and side edges 64 that extend between the inner and outer edges. Use of the relative terms inner and outer is intended to mean that the inner edges 62 are positioned closer to the transverse axis 24 of the undergarment 20. With particular reference to FIG. 2, the inner edges 62 may overlap the absorbent assembly 42 somewhat, while the outer edges 63 may be coterminous with the moisture barrier 40 and bodyside liner 44. Although the inner edges 62 are illustrated as being disposed between the bodyside liner 44 and the absorbent assembly 42, the inner edges 62 may alternatively be disposed between the absorbent assembly and the moisture barrier 40.

In one aspect of the invention, each moisture control layer 60 is adapted to accommodate liquid which can normally tend to form in the first or second waist regions 30 and 32. More precisely, each moisture control layer 60 comprises a material having a total water capacity sufficient to manage the quantity of liquid that is likely to result in a waist region 30 or 32 from condensation or perspiration. The moisture control layer 60 suitably has a total water capacity of at least about 0.5 gram, and more particularly from about 1 to about 15 grams, and more desirably from about 4 to about 15 grams, for improved performance. On a gram per gram basis, the moisture control layer 60 suitably has a total water capacity of at least about 3, more particularly at least about 4, and more desirably from about 5 to about 15. The total water capacity of a fabric can be determined according to the Total Water Capacity Test as set forth in the TEST PROCEDURES section below.

In addition to its liquid capacity, the moisture control layer 60 should be present over a sufficient portion of the area of the waist regions 30 or 32 to prevent localized portions of the waist regions from becoming uncomfortable. Thus, in another aspect of the invention, the moisture control layer 60 is present in from about 25 to 100 percent of the area of the first waist region 30 or the second waist region 32, and more particularly present in from about 50 to 100 percent of the area, and more desirably present in from about 70 to 100 percent of the area, for improved performance.

With further reference to FIG. 2, it can be seen that the moisture control layer 60 is positioned partially in the first waist region 30 and partially in the crotch region 34. The relevant portion of the moisture control layer 60 that lies exclusively in the first waist region 30 is the area defined between the outer edge 63 of the moisture control layer and the first end 42 of the absorbent assembly 42, and the full width of the moisture control layer. The length dimension of the portion of the moisture control layer 60 that is present in the first waist region 30 is equal to the length of the first waist region, which is labeled D1. In one particular embodiment, the first waist region 30 has an area of more than about 280 square centimeters, and the portion of the moisture control layer that is disposed exclusively in the first waist region has an area of more than about 130 square centimeters.

In another aspect of the invention, each moisture control layer 60 is adapted to limit the transport of liquid from the absorbent assembly 42 into the waist regions 30 and 32. In this way, the moisture control layer 60 may be in liquid contact with the absorbent assembly 42 as illustrated in FIGS. 1 and 2 without detrimentally effecting the dryness of the waist regions 30 and 32. Thus, in particular embodiments, each moisture control layer 60 has a liquid wicking rate of less than about 3 centimeters per 30 minutes, and particularly less than about 1 cm. per 30 minutes, and more desirably a liquid wicking rate 0 cm. per 30 minutes. The liquid wicking rate of a fabric can be determined according to the Liquid Wicking Test as set forth in the TEST PROCEDURES section below.

Figure 3:
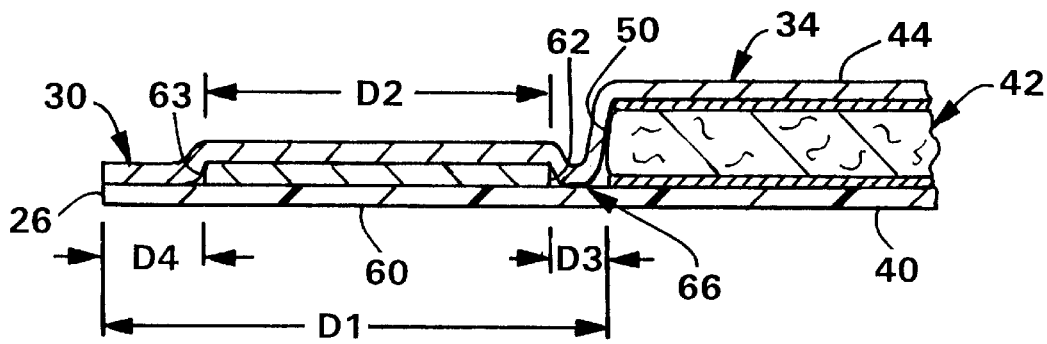
FIG. 3 representatively shows an enlarged section view similar to FIG. 2 but illustrating an alternative embodiment of the invention.

A modified position of the moisture control layer 60 is illustrated by an alternative embodiment partially shown in FIG. 3, where components similar to those previously described have the same reference numeral. Here, the moisture control layer 60 is disposed exclusively in the first waist region 30. The full length of the moisture control layer 60 is disposed in the first waist region 30 and designated D2. The inner edge 62 of the moisture control layer 60 is longitudinally separated from the absorbent assembly 42 by a gap 66 to further limit the transport of liquid from the absorbent assembly 42 into the waist region 30. The amount of the gap 66, measured parallel to the longitudinal axis 22 of the undergarment 20, is designated D3 in FIG. 3 and is suitably at least about 1 centimeter, such as at least about 2 centimeters. The gap 66 tends to limit the transport of liquid in instances where the bodyside liner 44 has a liquid wicking rate comparable to that of the moisture control layer 60. Specifically, the bodyside liner suitably has a liquid wicking rate of less than about 3 cm. per 30 minutes, and particularly less than about 1 cm. per 30 minutes, and more desirably a liquid wicking rate of 0 cm. per one half hour.

As further illustrated in FIG. 3, the outer edge 63 of the moisture control layer 60 may optionally be longitudinally separated from the first end edge 26. The outer edge 63 may, for example, be longitudinally separated from the first end edge 26 by a distance that is designated D4 in FIG. 3 of more than 1 centimeter. In the embodiment of FIG. 3, the length D1 of the first waist region 30 is equal to the sum of the length D2 of the moisture control layer 60, the amount D3 of the gap 66, and the spacing D4 from the first end edge 26.

Figure 4:
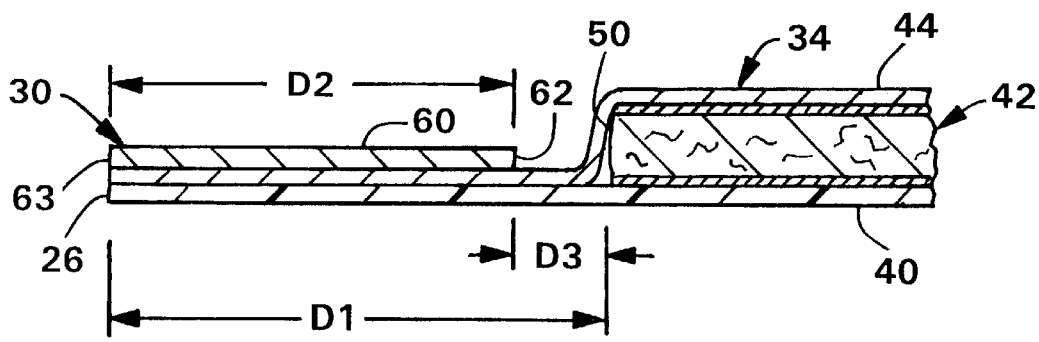
FIG. 4 representatively shows an enlarged section view similar to FIG. 2 but illustrating another alternative embodiment of the invention.

The moisture control layer 60 is illustrated in a further modified position in the alternative embodiment partially shown in FIG. 4. The moisture control layer 60 in FIG. 4 is disposed on the bodyside liner 44 so as to be in contact with the wearer when the undergarment 20 is worn. Specifically, the moisture control layer 60 is disposed immediately adjacent to and in contact with the bodyside liner 44, and the bodyside liner is disposed immediately adjacent to and in contact with the moisture barrier 40. In contrast, in FIGS. 1–3 the bodyside liner 44 is disposed immediately adjacent to and in contact with the moisture control layer 60, and the moisture control layer is disposed immediately adjacent to and in contact with the moisture barrier 40.

Figure 5:
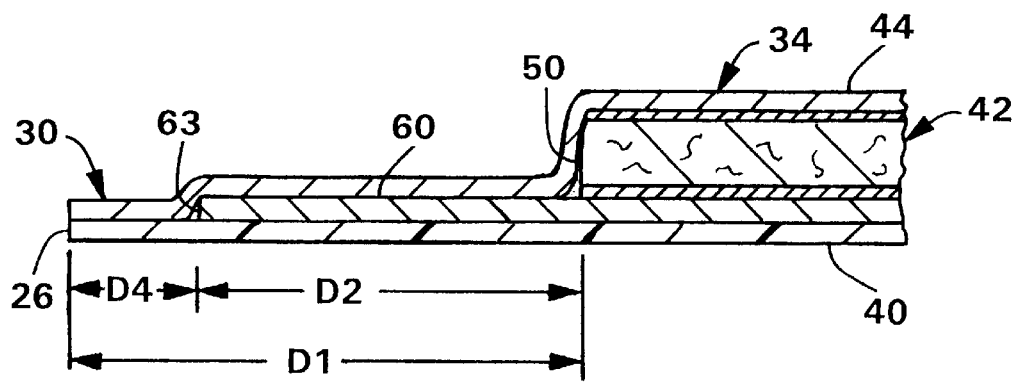
FIG. 5 representatively shows an enlarged section view similar to FIG. 2 but illustrating a further alternative embodiment of the invention.

A further alternative embodiment of the invention is partially illustrated in FIG. 5, where a single moisture control layer 60 extends substantially the full length of the undergarment 20 so as to be positioned in both the first and the second waist regions 30 and 32 (only 30 shown). In particular embodiments, the moisture control layer 60 may extend from about 80 to 100 percent of the distance between the first and second end edges 26 and 27. In the crotch region 34, the moisture control layer 60 may be disposed between the absorbent assembly 42 and the moisture barrier 40 as illustrated. Alternatively, the moisture control layer 60 may be disposed between the bodyside liner 44 and the absorbent assembly 42 in the crotch region 34. The single moisture control layer 60 has opposite longitudinal end edges 63 and side edges 64 (not shown in FIG. 5) that extend between the end edges. The length of the portion of the moisture control layer 60 that resides in the first waist region 30 is designated D2 and is defined between the first longitudinal end 50 of the absorbent assembly 42 and end edge 63 of the moisture control layer.

Due to its size and positioning, the moisture control layer 60 is desirably formed of a material that is substantially inelastic. The term "substantially inelastic" is intended to describe a material that is not elastomeric. The nonelastic properties of the moisture control layer 60 allow the waist regions 30 and 32 to lay comfortably against the abdomen or lower back of the wearer.

Desirably although not necessarily, the undergarment 20 also includes leg elastic members 70 to draw and hold the side margins 38 of the undergarment 20 against the legs of the wearer and form a seal therewith (FIG. 1). The elongated leg elastic members 70 are longitudinally orientated in each side margin 38, extending toward the first and second end edges 26 and 27. The leg elastic members 70 are positioned in the illustrated embodiment between the moisture barrier 40 and the bodyside liner 44. Using ultrasonic bonds, adhesives, thermal bonds, or other suitable means, the leg elastic members 70 are operatively joined in a stretched condition to the moisture barrier 40, the bodyside liner 44, or both, in either a straight or a curved shape. Alternatively, the leg elastic members 70 may be attached in a relaxed state to a gathered portion of the moisture barrier 40, the bodyside liner 44, or both.

The leg elastic members 70 may be formed of a dry-spun coalesced multifilament elastomeric thread sold under the tradename LYCRA and available from E.I. Du Pont de Nemours and Company. Alternately, the elastic members may be formed of other typical elastics utilized in the undergarment-making art, such as a thin ribbon of natural rubber, a stretch bonded laminate material comprising a prestretched elastic meltblown inner layer sandwiched between and bonded to a pair of spunbond polypropylene nonwoven webs, or the like. Elasticity could also be imparted to the absorbent article by extruding a hot melt elastomeric adhesive between the moisture barrier 40 and the liner 44. Other suitable elastic gathering means are disclosed in U.S. Pat. No. 4,938,754 to Mesek and U.S. Pat No. 4,388,075 to Mesek et al.

The undergarment 20 may be maintained in position against the wearer as a result of being placed within the underpants of the wearer. Optionally, the undergarment 20 may employ any one of a number of attachment systems as are well known in the art to secure the product in place against the wearer. By way of illustration, one desirable form of attachment system comprises a pair of strap members and fastening components to releasably attach the strap members to the first and second waist regions 30 and 32. Suitable strap members may comprise generally rectangular strips of an elastic material that is capable of stretching to approximately 2.8 to 3 times its relaxed length. The strap members desirably have a length from about 15 to about 41 centimeters, and a width from about 1 to about 5 centimeters. The fastening components may comprise a retainer in the form of a button bonded at each end of each strap member. The retainers may be releasably secured in slits 72 (FIG. 1) formed near the corners of the undergarment 20 in the moisture barrier 40 and other components. When the undergarment 20 is positioned on the wearer, the straps extend between the front and back slits 72 so that the retainers may be releasably secured in the slits. Attachment systems of the foregoing type are illustrated in U.S. Pat. No. 4,315,508 issued Feb. 16, 1982 to Bolick; U.S. Pat. No. 4,886,512 issued Dec. 12, 1989 to Damico et al.; and U.S. Pat. No. 4,904,249 issued Feb. 27, 1990 to Miller et al.; the disclosures of which are incorporated herein by reference.

Optionally, the fastening components may comprise fasteners with self-engaging geometric shaped materials. Suitable fasteners of this type include hooks, loops, bulbs, mushrooms, arrowheads, balls on stems, or the like. Fastening systems of this type that are particularly desirable for use on an undergarment are illustrated in U.S. Pat. No. 5,386,595 issued Feb. 7, 1995 to Kuen et al.; U.S. Pat. No. 5,304,162 issued Apr. 19, 1994 to Kuen; U.S. Pat. No. 4,847,134 issued Jul. 11, 1989 to Fahrenkrug et al.; U.S. Pat. No. 5,374,262 issued Dec. 20, 1994 to Keuhn, Jr. et al.; and U.S. patent application Ser. No. 08/366,077 filed Dec. 28, 1994 by Datta et al. and assigned to the assignee of the present application; the disclosures of which are incorporated herein by reference. Still optionally, other types of attachment systems, such as tapes, stretchable side panels, or the like, may be employed. Examples of other such attachment systems are illustrated in U.S. Pat. No. 4,500,316 issued Feb. 19, 1985 to Damico; and U.S. Pat. No. 5,411,498 issued May 2, 1995 to Fahrenkrug et al.; the disclosure of which is incorporated herein by reference.

In use, the undergarment 20 is positioned on the body of the wearer and secured in position using the attachment system, if any. The moisture control layer 60 is desirably although not necessarily disposed in both waist regions 30 and 32 of the undergarment 20 so as to be located adjacent the abdomen and lower back of the wearer. The moisture control layer 60 can accommodate liquid which forms in the waist regions 30 and 32 as a result of condensation or perspiration. The moisture control layer 60 also reduces the incidence of liquid from the absorbent assembly 42 wicking into the waist regions 30 and 32. By reducing the flow of liquid into the waist regions 30 and 32 from the absorbent assembly 42, the moisture control layer 60 retains its liquid capacity for accommodating condensation and perspiration. As a result, the waist regions 30 and 32 of the undergarment will feel dry and comfortable against the skin of the wearer.

Each of the foregoing embodiments of the undergarment 20 may be constructed by providing each of the individual components and bonding them together in the manner set forth above. In each of the embodiments, the moisture control layer 60 may be placed in the waist regions 30 and/or 32 by providing a moisture control material, cutting the material to the desired size, and bonding the material to the other components.

Figure 1A:
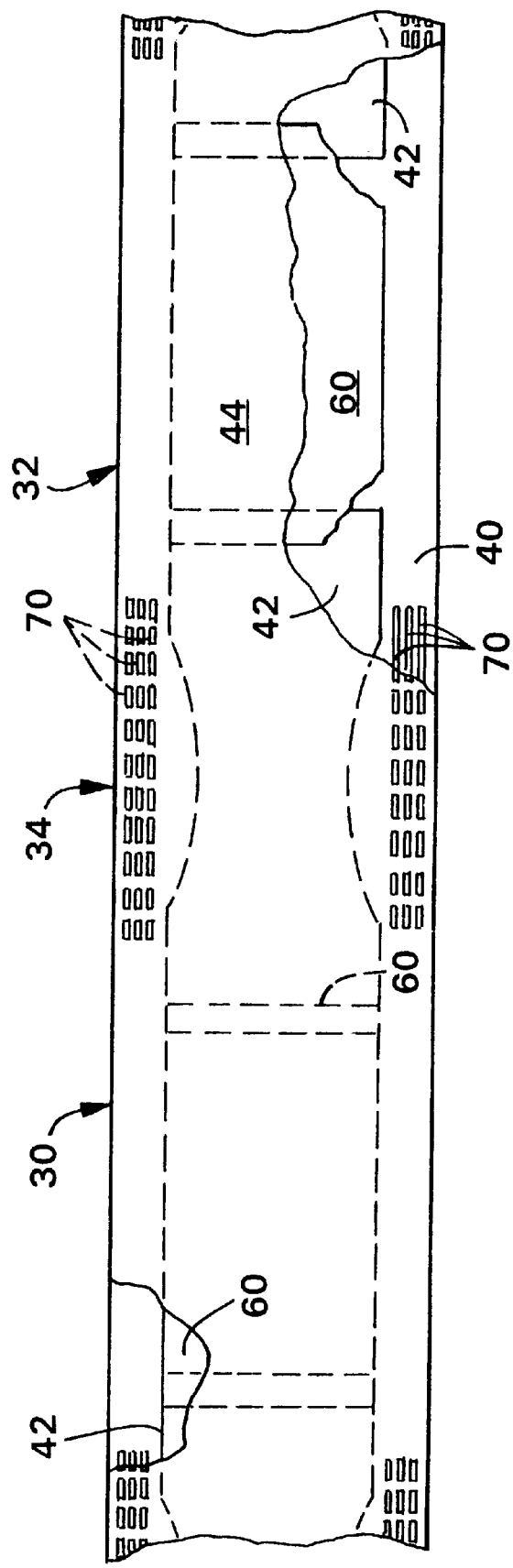
FIG. 1A representatively shows a plan view illustrating a method for producing the absorbent article of FIG. 1.

One particularly efficient method for producing undergarments 20 of the type illustrated in FIGS. 1–2 and 4, where the outer edge 63 of the moisture control layer 60 is coincident with the end edge 26 or 27 of the moisture barrier 40, is also available and is illustrated in FIG. 1A. This method places the moisture control layer 60 in the waist regions 30 and 32 using a continuous processes. In particular, the method includes providing a first continuous web of the liquid impermeable moisture barrier 40. A plurality of absorbent assemblies 42 are disposed on the moisture barrier at predetermined, spaced locations. The method also includes providing a plurality of individual sheets of material to form the moisture control layers 60 of the undergarments 20. The moisture control sheets 60 are disposed on the continuous moisture barrier web 40 at locations between the neighboring absorbent assemblies 42. The method further includes providing a second continuous web of the liquid permeable bodyside liner 44. The continuous moisture barrier web 40, the continuous bodyside liner web 44, and the sheets of moisture control material 60 are bonded together with the absorbent assemblies 42 disposed between the moisture barrier and bodyside liner webs. Subsequently, the continuous moisture barrier web 40, the continuous bodyside liner web 44, and the sheets of moisture control material 60 are transversely cut at a series of spaced locations between the neighboring absorbent assemblies 42. The result is a plurality of individual undergarments 20, each having an absorbent assembly 42 disposed between a bodyside liner 44 and a moisture barrier 40. The spacing of the components and the position of the transverse cuts can be controlled so that one or both of the waist regions 30 or 32 have a length dimension greater than about 10 centimeters and the moisture control material 60 is present in from about 25 to 100 percent of the area of the waist region.

TEST PROCEDURES

Total Water Capacity Test

The Total Water Capacity test is designed to determine the capacity of a material to absorb distilled water. In general, a dry specimen is weighed, immersed in the liquid for 3 minutes and then hung up to allow excess liquid to drain off. The wet specimen is then weighed again. The total water capacity of the specimen is the wet weight minus the dry weight of the specimen. The absorption capacity of nonwoven fabrics can be reported as a gram per gram value, which is the total capacity divided by the dry weight of the specimen, or as a percent absorption, which is the total capacity times 100 divided by the dry weight.

The test employs the following equipment and materials:
1. Laboratory stand and rod.
2. Spring clamps, 1 inch (25 mm) or larger.
3. Distilled water at room temperature.
4. Pan large enough to hold the distilled water to a depth of at least 102 mm.
5. Balance, readable to 0.01 grams. A device designated PM300 available from Mettler Instrument Corp., Hightstown, N.J., for example, or an equivalent.
6. Calibration weights, 5, 10, 20, 50, 100 grams, traceable to the National Institute of Standards and Technology.
7. Weighing dish, metal or plastic, with at least a 4 inch (102 mm) diameter.
8. Stopwatch or timer, readable to one second.
9. Tongs or tweezers.
10. Paper toweling.
11. Paper cutter, standard, 300 by 300 mm minimum cutting area with grid lines.
    Available from Testing Machines Inc., Amityville, N.Y. 11701, for example, or an equivalent.

The test should be conducted in a room with a standard-condition atmosphere: temperature=23±10° C. (73.4+1.80° F.) and relative humidity=50±2%. Testing outside the specified limits for temperature and humidity may not yield valid results.

The material to be tested should be cut into specimens measuring 102 by 102 mm. The specimens should be handled only by the edges and should be absolutely dry. As much as possible, avoid pressing the surface of the specimens while cutting. The following other precautions should be observed:

1. The drop of liquid that is suspended from the specimen at the end of the draining time should be "caught" on the weighing dish to be weighed with the specimen.
2. The specimen should lie entirely within the weighing dish. Make sure that the specimen does not touch the sides or the flat part of the balance while it is being weighed.
3. Do not shake the table or the specimens while they are draining.
4. Samples must be conditioned at the standard temperature and humidity.
5. The number of specimens that may be tested at one time is dependent upon the size of the pan being used.
6. The smoothest side of the specimen should be gently placed on the surface of the water before submerging.

The equipment is then set up in the following manner. Equipment manufacturers or their literature should be consulted for specific calibration information.

1. Turn on the balance and allow a warm-up time. Tare the balance to zero.
2. Fill the pan with the distilled water to a depth of at least 102 mm.
3. Assemble the laboratory stand and rod.

Each specimen is then tested according to the following procedure:

1. Weigh each specimen to the nearest 0.01 gram and record this value. Retain the identification of each specimen.
2. Simultaneously start the timer and drop the specimens, one at a time, into the distilled water. The specimens should be evenly spaced apart and not on top of one another. On creped wadding, make sure each specimen is completely submerged before putting in the next one.
3. Each specimen is left in the liquid for 3 minutes±3 seconds.
4. At 3 minutes, remove the first specimen with the tongs or tweezers and suspend vertically from the spring clamp. Remove and suspend the remaining specimens in the same order they were put into the pan.
5. Each specimen is drained 1 minute±3 seconds.
6. Put the weighing dish on the scale and tare to zero.
7. Remove the specimen by holding the weighing dish under the specimen and releasing the clamp.
8. Weigh the wet specimen to the nearest 0.01 gram. Record this value next to the corresponding dry weight value. The wet specimen may not be left on the weighing dish.

9. Tare the balance to zero and repeat steps 7 and 8 for each specimen. Specimens must be weighed in the same order as they were put in the liquid.

10. Remove the wet specimens and wipe the weighing dish between each set of specimens.

Using the individual dry and wet weights recorded for each specimen, the following calculations may be made. Calculate to the nearest 0.01 gram for each specimen.

$$\text{Total Capacity (gm)} = \text{wet weight (gm)} - \text{dry weight (gm)}.$$

$$\text{Percent Absorption} = \frac{\text{Total Capacity} \times 100}{\text{Dry Weight}}$$

$$\text{Gram per Gram Absorption} = \frac{\text{Total Capacity}}{\text{Dry Weight}}$$

Liquid Wicking Test

Figure 6:
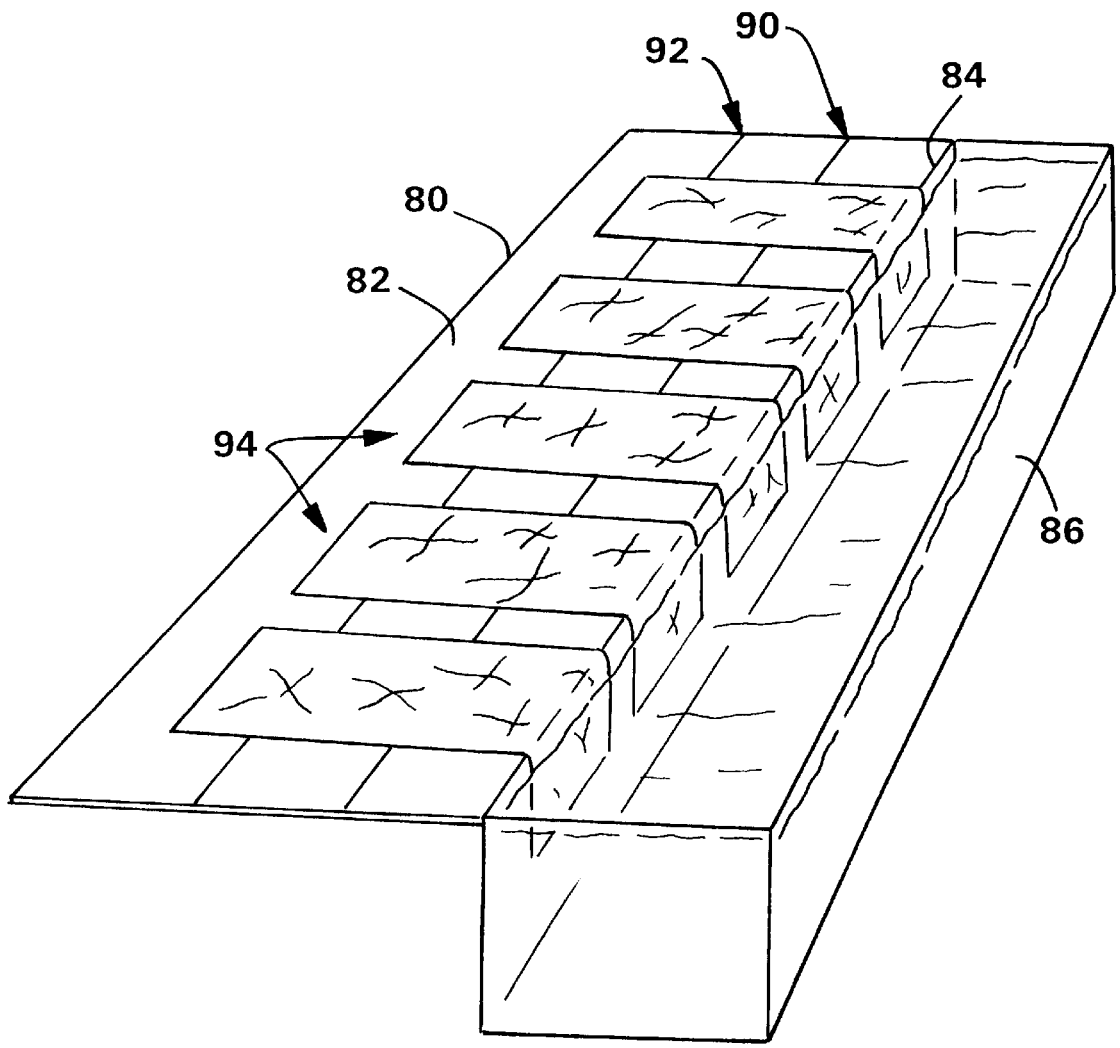
FIG. 6 representatively shows the test structure for measuring a liquid wicking rate of a material.

The Wicking test measures the lateral movement of room temperature-distilled water through a material which is supported by a vinyl coated stainless steel plate. The plate 80, which is shown in FIG. 6, has a top surface 82 with an edge 84. A container 86 of distilled water is positioned beneath the edge 84 of the plate 80 such that the distance between the top surface and the water level is 1 cm. The plate 80 has lines 90 and 92 marking 5 and 10 cm., respectively, from the edge 84 of the plate.

In the test, five 50.8 by 152.4 mm. specimens 94 of the material to be tested are mounted on the top surface of the level plate. An end of each specimen is weighted and positioned over the edge of the plate and into the liquid. When the sample ends are dropped into the liquid, a timer is started.

The progress of the liquid front is observed and the time, measured to the nearest 0.1 minute, is recorded as the liquid front begins to cross 5 and 10 cm. marks. If the liquid front has not reached the 10 cm. mark in 30 minutes, the test is stopped and maximum distance is recorded. The wicking value for a material is the average distance traveled after 30 minutes by the 5 specimens tested.

Saturated Retention Capacity Test The saturated retention capacity of a material is measured as follows. The material to be tested, having a moisture content of less than about 7 weight percent, is weighed and submerged in an excess quantity of room temperature (about 23 degrees Celsius) synthetic urine. The material to be tested is allowed to remain submerged for 20 minutes. After 20 minutes, the material is removed from the urine and placed on a TEFLON® coated fiberglass screen having 0.25 inch openings (commercially available from Taconic Plastics Inc., Petersburg, N.Y.) which, in turn, is placed on a vacuum box and covered with a flexible rubber dam material. A vacuum of 3.5 kilopascals (0.5 pounds per square inch) is drawn in the vacuum box for a period of 5 minutes. The material is weighed. The amount of fluid retained by the material being tested is determined by subtracting the dry weight of the material from the wet weight of the material (after application of the vacuum) and is reported as the saturated retention capacity in grams of fluid retained. For relative comparisons, this value can be divided by the weight of the material to give the saturated retention capacity in grams of fluid retained per gram of tested material.

The synthetic urine composition referenced herein comprises 0.31 grams monobasic calcium phosphate monohydrate (CaH4(PO4)2H2O), 0.68 grams monobasic potassium phosphate (KH2PO4), 0.48 grams magnesium sulphate heptahydrate (MgSO4 7H2O), 1.33 grams potassium sulphate (K2SO4), 1.24 grams tribasic sodium phosphate dodecahydrate (Na3PO4 12H2O), 4.4 grams sodium chloride (NaCl), 3.16 grams potassium chloride (KCl), 8.56 grams of urea (CO(NH2)2), 0.1 grams Pluronic 10R8 surfactant (a nonionic surfactant commercially available from BASF-Wyandotte Corporation) and 1 gram methyl paraben and 1 gram Germall 115 preservative (commercially available from Santell Chemical Company, Chicago, Ill.) per liter using distilled water as the solvent. The components are added to 900 milliliters of distilled water in the order given and each dissolved before the next component is added. The solution is finally diluted to one liter.

If material, such as high-absorbency material or fiber is drawn through the fiberglass screen while on the vacuum box, a screen having smaller openings should be used. Alternatively, a piece of tea bag material can be placed between the material and the screen and the final value adjusted for the fluid retained by the tea bag material. Suitable tea bag material is a heat sealable tea bag material grade 542, commercially available from Kimberly-Clark Corporation. The amount of fluid absorbed by the tea bag material is determined by performing the saturated retention capacity test on an empty tea bag. Testing high-absorbency materials or fibers alone can be accomplished using a sealed pouch of tea bag material.

Water Vapor Transmission Rate Test

A suitable technique for determining the WVTR (water vapor transmission rate) value of a material is ASTM Standard E96-80. For the purposes of the present invention, circular samples measuring 3 inches in diameter are cut from the test material and a control material which is a piece of CELGUARD® 2500 film from Hoechst Celanese Corporation of Sommerville, N.J., USA. CELGUARD® 2500 is a 0.0025 cm thick microporous polypropylene film.

Five samples are prepared for each material. The test dish is a No. 60-1 Vapometer pan distributed by Thwing-Albert Instrument Company, Philadelphia, Pa., U.S.A. One hundred milliliters of water are poured into each Vapometer pan, and each of the samples of the test material and control material are placed across the open tops of the individual pans. Do not apply stopcock grease unless sample contamination can be avoided. Screw-on flanges are tightened to form a seal along the edges of the pans, leaving the associated test material or control material exposed to the ambient atmosphere over a 6.5 cm diameter circle having an exposed area of about 33.17 square centimeters. The pans are placed in a forced air oven set at 32° C. (100° F.) for 1 hour to equilibrate. The oven is a constant temperature oven with external air circulating through it to prevent water vapor accumulation inside. A suitable forced air oven is, for example, a Blue M Power-O-Matic 60 oven distributed by Blue M Electric Co. of Blue Island, Ill., U.S.A. Upon completion of the equilibration, the pans are removed from the oven, weighed and immediately returned to the oven. After 24 hours, the pans are removed from the oven and weighed again. The preliminary test WVTR value is calculated as follows:

Test WVTR=(grams weight loss over 24 hours)×315.5 (g/m²/24 hours)

The relative humidity within the oven is not specifically controlled.

Under predetermined set conditions of 32° C. (100° F.) and ambient relative humidity, the WVTR for CELGUARD® 2500 has been determined to be 5000 gm/m²/24 hours. Accordingly, the CELGUARD® 2500 is run as a control sample with each test, and the preliminary test values are corrected to the set conditions using the following equation:

WVTR=(Test WVTR/control WVTR)×5000 gm/m²/24 hr.

EXAMPLES

The following EXAMPLES are provided to give a more detailed understanding of the invention. The particular amounts, proportions, compositions and parameters are meant to be exemplary, and are not intended to specifically limit the scope of the invention.

Example A (Comparative Example)

An absorbent article was produced comprising a liquid impermeable moisture barrier, a liquid permeable bodyside liner, and an absorbent assembly disposed between the moisture barrier and the bodyside liner. These components were bonded together using a construction adhesive.

The moisture barrier comprised a polyethylene film having a nominal thickness of about 0.025 millimeter, a systematic matte embossed pattern, and corona treating on both sides. The moisture barrier was rectangular with a length of 69 cm. and a width of 22.1 cm.

The absorbent assembly was disposed on the moisture barrier and equally spaced between the end edges of the moisture barrier. The absorbent assembly included an absorbent batt formed of cellulose fluff, sprayed polypropylene filaments, and high-absorbency particles and had an estimated saturated liquid retention capacity of 450 grams. The absorbent assembly included a 22 gsm tissue layer over the top surface of the absorbent batt. Both the absorbent batt and the tissue had a length of 43.2 cm. The absorbent batt had a width which varied between 11.6 cm. near the center and 14 cm. at the ends, and the tissue had a width of 22 cm.

The bodyside liner was disposed on the absorbent assembly and the moisture barrier. The bodyside liner comprised a nonwoven, spunbond polypropylene fabric composed of about 2.8–3.2 denier fibers formed into a web having a basis weight of about 17 gsm and density of about 0.11 gm/cc. The fabric was surface treated with about 0.28 weight percent of a surfactant commercially available under the trade designation Triton X-102 from Union Carbide Chemicals and Plastics Company, Inc. of Danbury, Conn., U.S.A. The bodyside liner had a liquid wicking rate of 0 cm. per 30 minutes, and a total water absorption capacity of 0.56 gram (3.18 grams/gram). The bodyside liner was rectangular with the same dimensions as the moisture barrier.

Both waist regions of the absorbent article had a length of about 12.7 cm. and a width of 22.1 cm. In the waist regions, the bodyside liner was disposed immediately adjacent to and in contact with the moisture barrier over the full area of the waist regions.

Example B (Comparative Example)

An absorbent article was produced comprising a liquid impermeable moisture barrier, a liquid permeable bodyside liner, and an absorbent assembly disposed between the moisture barrier and the bodyside liner. These components were bonded together using a construction adhesive. The moisture barrier and the bodyside liner were formed of the same materials and had the same sizes as those in Example A.

The absorbent assembly was disposed on the moisture barrier and equally spaced between the end edges of the moisture barrier. The absorbent assembly included an absorbent batt formed of cellulose fluff, sprayed polypropylene filaments, and high-absorbency particles and had an estimated saturated liquid retention capacity of 450 grams. The absorbent assembly included a 22 gsm tissue layer over the top surface of the absorbent batt. Both the absorbent batt and the tissue had a length of 43.2 cm. The absorbent batt had a width which varied between 11.6 cm near the center and 14 cm near the ends, and the tissue had a width of 16 cm. The absorbent balt was formed of the same materials and was the same size as the absorbent batt in Example A.

The absorbent article also included a full length, single layer of tissue positioned over the top surface of the absorbent batt so as to be disposed between the bodyside liner and the absorbent batt. The full-length tissue had a basis weight of about 22 grams, a length of 69 cm., and a width of 16 cm.

Both waist regions of the absorbent article had a length of about 12.7 cm. and a width of 22.1 cm. In the waist regions, the bodyside liner was disposed immediately adjacent to and in contact with the full length tissue, and the full length tissue was disposed immediately adjacent to and in contact with the moisture barrier. The full-length tissue was present in about 72 percent of the area of each waist region.

Example C

An absorbent article was produced comprising a liquid impermeable moisture barrier, a liquid permeable bodyside liner, and both an absorbent assembly and a moisture control layer disposed between the moisture barrier and the bodyside liner. These components were bonded together using a construction adhesive. The moisture barrier and the bodyside liner were formed of the same materials and had the same sizes as those in Example A.

The absorbent assembly included an absorbent batt that was formed of the same materials and was the same size as the absorbent batt in Example A. The absorbent assembly did not include any layers of tissue.

The moisture control layer comprised a single web of material that was positioned over the top surface of the absorbent batt so as to be disposed between the bodyside liner and the absorbent batt. The moisture control layer comprised a nonwoven, spunbond polypropylene fabric composed of about 2.8–3.2 denier fibers formed into a web having a basis weight of about 36 gsm and density of about 0.12 gm/cc. The fabric was surface treated with about 0.3 weight percent of a surfactant commercially available under the trade designation Triton X-102 from Union Carbide Chemicals and Plastics Company, Inc. The moisture control layer was rectangular with a length of 69 cm. and a width of 10.8 cm.

Both waist regions of the absorbent article had a length of about 12.7 cm. and a width of 22.1 cm. In the waist regions, the bodyside liner was disposed immediately adjacent to and in contact with the moisture control layer, and the moisture control layer was disposed immediately adjacent to and in contact with the moisture barrier. The moisture control layer was present in about 49 percent of the area of each waist region.

Example D

An absorbent article was produced comprising a liquid impermeable moisture barrier, a liquid permeable bodyside liner, and both an absorbent assembly and a moisture control layer disposed between the moisture barrier and the bodyside liner. These components were bonded together using a construction adhesive. The moisture barrier and the bodyside liner were formed of the same materials and had the same sizes as those in Example A, and the absorbent assembly was formed of the same materials and was the same size as the absorbent assembly in Example C.

The moisture control layer comprised two webs of material that were disposed between the bodyside liner and the moisture barrier in the waist regions. The moisture control layer comprised webs formed of the same material as the moisture control layer in Example C. The webs were both rectangular with a length of 12.7 cm. and a width of 10.8 cm., with the webs positioned so as to overlap the absorbent assembly by less than about 1 cm.

Both waist regions of the absorbent article had a length of about 12.7 cm. and a width of 22.1 cm. In the waist regions, the bodyside liner was disposed immediately adjacent to and in contact with the moisture control layer, and the moisture control layer was disposed immediately adjacent to and in contact with the moisture barrier. The moisture control layer was present in about 49 percent of the area of each waist region.

Example E

An absorbent article was produced comprising a liquid impermeable moisture barrier, a liquid permeable bodyside liner, and both an absorbent assembly and a moisture control layer disposed between the moisture barrier and the bodyside liner. These components were bonded together using a construction adhesive. The moisture barrier and the bodyside liner were formed of the same materials and had the same sizes as those in Example A, and the absorbent assembly was formed of the same materials and was the same size as the absorbent assembly in Example C.

The moisture control layer comprised a single web of material that was positioned over the top surface of the absorbent batt so as to be disposed between the bodyside liner and the absorbent batt. The moisture control layer comprised a nonwoven, fabric composed of a homogeneous blend of 70 percent 2.8 denier polypropylene fibers and 30 percent 6 denier polyester fibers. Suitable polypropylene fibers are available under the trade designation T-196 from Hercules Inc. of Wilmington, Del., U.S.A. Suitable polyester fibers are available under the trade designation T-295 from Hoechst Celanese Corporation of Sommerville, N.J., USA. The fibers were carded into a web having a basis weight of about 50 gsm and through-air-bonded. The fibers have a finish treatment to enhance wettability. The moisture control layer was rectangular with a length of 69 cm. and a width of 16 cm.

Both waist regions of the absorbent article had a length of about 12.7 cm. and a width of 22.1 cm. In the waist regions, the bodyside liner was disposed immediately adjacent to and in contact with the moisture control layer, and the moisture control layer was disposed immediately adjacent to and in contact with the moisture barrier. The moisture control layer was present in about 72 percent of the area of each waist region.

Example F

An absorbent article was produced comprising a liquid impermeable moisture barrier, a liquid permeable bodyside liner, and both an absorbent assembly and a moisture control layer disposed between the moisture barrier and the bodyside liner. These components were bonded together using a construction adhesive. The moisture barrier and the bodyside liner were formed of the same materials and had the same sizes as those in Example A, and the absorbent assembly was formed of the same materials and was the same size as the absorbent assembly in Example B.

The moisture control layer comprised two webs of material that were disposed between the bodyside liner and the moisture barrier in the waist regions. The moisture control layer comprised webs formed of the same material as the moisture control layer in Example E. The webs were both rectangular with a length of 12.7 cm. and a width of 16 cm., with the webs positioned so as to overlap the absorbent assembly by less than about 1 cm.

Both waist regions of the absorbent article had a length of about 12.7 cm. and a width of 22.1 cm. In the waist regions, the bodyside liner was disposed immediately adjacent to and in contact with the moisture control layer, and the moisture control layer was disposed immediately adjacent to and in contact with the moisture barrier. The moisture control layer was present in about 72 percent of the area of each waist region.

Example G

An absorbent article was produced comprising a liquid impermeable moisture barrier, a liquid permeable bodyside liner, and both an absorbent assembly and a moisture control layer disposed between the moisture barrier and the bodyside liner. These components were bonded together using a construction adhesive. The moisture barrier and the bodyside liner were formed of the same materials and had the same sizes as those in Example A, and the absorbent assembly was formed of the same materials and was the same size as the absorbent assembly in Example C.

The moisture control layer comprised a single web of material that was positioned over the top surface of the absorbent batt so as to be disposed between the bodyside liner and the absorbent batt. The moisture control layer comprised a nonwoven, fabric composed of a homogeneous blend of 60 percent 3 denier polyethylene/polypropylene bicomponent fibers and 40 percent 6 denier polyester fibers. Suitable bicomponent fibers are available under the trade designation ESC-HR5 from Chisso Corporation of Osaka, Japan. Suitable polyester fibers are available under the trade designation T-295 from Hoechst Celanese Corporation of Sommerville, N.J., USA. The fibers were carded into a web having a basis weight of about 50 gsm and through-air-bonded. The fibers were treated with a finish to enhance wettability. The moisture control layer was rectangular with a length of 69 cm. and a width of 13 cm.

Both waist regions of the absorbent article had a length of about 12.7 cm. and a width of 22.1 cm. In the waist regions, the bodyside liner was disposed immediately adjacent to and in contact with the moisture control layer, and the moisture control layer was disposed immediately adjacent to and in contact with the moisture barrier. The moisture control layer was present in about 59 percent of the area of each waist region.

Example H

An absorbent article was produced comprising a liquid impermeable moisture barrier, a liquid permeable bodyside liner, and both an absorbent assembly and a moisture control layer disposed between the moisture barrier and the bodyside liner. These components were bonded together using a construction adhesive. The moisture barrier and the bodyside liner were formed of the same materials and had the same sizes as those in Example A, and the absorbent assembly was formed of the same materials and was the same size as the absorbent assembly in Example C.

The moisture control layer comprised two webs of material that were disposed between the bodyside liner and the moisture barrier in the waist regions. The moisture control layer comprised webs formed of the same material as the moisture control layer in Example G. The webs were both rectangular with a length of 12.7 cm. and a width of 13 cm., with the webs positioned so as to overlap the absorbent assembly by less than about 1 cm.

Both waist regions of the absorbent article had a length of about 12.7 cm. and a width of 22.1 cm. In the waist regions, the bodyside liner was disposed immediately adjacent to and in contact with the moisture control layer, and the moisture control layer was disposed immediately adjacent to and in contact with the moisture barrier. The moisture control layer was present in about 59 percent of the area of each waist region.

Example I

An absorbent article was produced comprising a liquid impermeable moisture barrier, a liquid permeable bodyside liner, and both an absorbent assembly and a moisture control layer disposed between the moisture barrier and the bodyside liner. These components were bonded together using a construction adhesive. The moisture barrier and the bodyside liner were formed of the same materials and had the same sizes as those in Example A, and the absorbent assembly was formed of the same materials and was the same size as the absorbent assembly in Example C.

The moisture control layer comprised a single web of material that was positioned over the top surface of the absorbent batt so as to be disposed between the bodyside liner and the absorbent batt. The moisture control layer comprised a nonwoven, fabric composed of a homogeneous blend of 60 percent 3 denier polyethylene/polypropylene bicomponent fibers and 40 percent 6 denier polyester fibers. Suitable bicomponent fibers are available under the trade designation ESC-HR5 from Chisso Corporation of Osaka, Japan. Suitable polyester fibers are available under the trade designation T-295 from Hoechst Celanese Corporation of Sommerville, N.J., USA. The fibers were carded into a web having a basis weight of about 100 gsm and through-air-bonded. The fibers were treated with a finish to enhance wettability. The moisture control layer was rectangular with a length of 69 cm. and a width of 10 cm.

Both waist regions of the absorbent article had a length of about 12.7 cm. and a width of 22.1 cm. In the waist regions, the bodyside liner was disposed immediately adjacent to and in contact with the moisture control layer, and the moisture control layer was disposed immediately adjacent to and in contact with the moisture barrier. The moisture control layer was present in about 45 percent of the area of each waist region.

Example J

An absorbent article was produced comprising a liquid impermeable moisture barrier, a liquid permeable bodyside liner, and both an absorbent assembly and a moisture control layer disposed between the moisture barrier and the bodyside liner. These components were bonded together using a construction adhesive. The moisture barrier and the bodyside liner were formed of the same materials and had the same sizes as those in Example A, and the absorbent assembly was formed of the same materials and was the same size as the absorbent assembly in Example C.

The moisture control layer comprised two webs of material that were disposed between the bodyside liner and the moisture barrier in the waist regions. The moisture control layer comprised webs formed of the same material as the moisture control layer in Example I. The webs were both rectangular with a length of 12.7 cm. and a width of 10 cm., with the webs positioned so as to overlap the absorbent assembly by less than about 1 cm.

Both waist regions of the absorbent article had a length of about 12.7 cm. and a width of 22.1 cm. In the waist regions, the bodyside liner was disposed immediately adjacent to and in contact with the moisture control layer, and the moisture control layer was disposed immediately adjacent to and in contact with the moisture barrier. The moisture control layer was present in about 45 percent of the area of each waist region.

Example K (Comparative Example)

A disposable undergarment sold by The Procter & Gamble Company under the trademark ATTENDS® was examined for purposes of comparison. The undergarment was taken from a bag of undergarments purchased in New Jersey in about February of 1995 and bearing the identification code 003700068456. The undergarment comprised a liquid impermeable moisture barrier, a liquid permeable bodyside liner, an absorbent assembly disposed between the moisture barrier and the bodyside liner, layers of toweling, and leg elastic members secured along the side margins of the undergarment. The undergarment also included button hole reinforcing tapes near the corners. The components of the undergarment appear to have been bonded together using a construction adhesive.

The moisture barrier is believed to comprise a polyethylene film. The moisture barrier was rectangular with a length of 71 cm. and a width of 21 cm.

The absorbent assembly was disposed on the moisture barrier and approximately equally spaced between the end edges of the moisture barrier. The absorbent assembly is believed to comprise an absorbent batt formed of cellulose fluff and high-absorbency particles. The absorbent assembly was determined to have a saturated liquid retention capacity of about 625 grams. The absorbent assembly was generally rectangular with a length of 46 cm. and a width of 11 cm.

The undergarment included several layers of heavy toweling. The toweling measured 20 cm. wide by 16 cm. long and was placed in each waist region. About 13 cm. of the length of the toweling was located in each waist region, with about 3 cm. of the length overlapping the absorbent assembly.

The bodyside liner was disposed on the absorbent assembly and the moisture barrier. The bodyside liner is believed to comprise a nonwoven, spunbond polypropylene fabric having a basis weight of about 28 gsm. The fabric is believed to be treated with a surfactant. The bodyside liner was rectangular with the same dimensions as the moisture barrier.

Both waist regions of the absorbent article had a length of about 13 cm. and a width of 21 cm. In the waist regions, the bodyside liner was disposed immediately adjacent to and in contact with the tissue, and the tissue was disposed immediately adjacent to and in contact with the moisture barrier. The tissue was present in about 95 percent of the area of each waist region.

Example N (Comparative Example)

An absorbent article was produced comprising a liquid impermeable moisture barrier, a liquid permeable bodyside liner, an absorbent assembly disposed between the moisture barrier and the bodyside liner, and an acquisition layer disposed between the absorbent assembly and the bodyside liner. The undergarment also included leg elastic members secured along the side margins of the undergarment and button hole reinforcing tapes near the corners. These components were bonded together using a construction adhesive.

The moisture barrier comprised a laminate of a breathable film stretched and thermally laminated to a polypropylene nonwoven cover. The moisture barrier measured 63.5 cm. by 22.3 cm.

The absorbent assembly comprised a mixture of 20.8 grams of fluff and 5.5 grams high-absorbency particles. The absorbent assembly measured 54.7 cm. by 15 cm., and a tissue was disposed over the absorbent assembly. The absorbent assembly was determined to have a saturated liquid retention capacity of about 423 grams.

The acquisition layer comprised a single web of material that was positioned over the top surface of the absorbent balt so as to be disposed between the bodyside liner and the absorbent batt. The acquisition layer comprised a nonwoven, fabric composed of a homogeneous blend of 50 percent 3 denier polypropylene fibers and 50 percent 6 denier polyester fibers. Suitable polypropylene fibers are available under the trade designation T-170 from Hercules Inc. of Wilmington, Del., U.S.A. Suitable polyester fibers are available under the trade designation T-295 from Hoechst Celanese Corporation of Sommerville, N.J., USA. The fibers were carded into a web having a basis weight of about 50 gsm and thermally bonded in a hexagonal patter. The fabric was surface treated with a surfactant commercially available under the trade designation Triton X-102 from Union Carbide Chemicals and Plastics Company, Inc. The acquisition layer was rectangular with a length of 63.5 cm. and a width of 7.6 cm.

The bodyside liner comprised a 17 gsm polypropylene spunbond web.

Both waist regions of the absorbent article had a length of about 4.4 cm. and a width of 22.3 cm. In the waist regions, the bodyside liner was disposed immediately adjacent to and in contact with the acquisition layer, and the acquisition layer was disposed immediately adjacent to and in contact with the moisture barrier. The acquisition layer was present in about 34 percent of the area of each waist region.

Example M1 (Comparative Example)

An absorbent article was produced comprising a liquid impermeable moisture barrier, a liquid permeable bodyside liner, and an absorbent assembly disposed between the moisture barrier and the bodyside liner. Two treated tissues were disposed in the waist regions. These components were bonded together using a construction adhesive. The moisture barrier and the bodyside liner were formed of the same materials and had the same sizes as those in Example A, and the absorbent assembly was formed of the same materials and was the same size as the absorbent assembly in Example C.

The treated tissues comprised a single ply uncreped throughdried tissue having solidified deposits formed thereon. The solidified deposits comprised 18% cerisin wax, 18% cetearyl alcohol, 1% dimethicone, 3% isopropyl palmitate, 0.1% vitamin E acetate, 0.1% aloe vera lipo quinone, and 59.8% mineral oil. Such tissues are described in U.S. patent application Ser. No. 08/384,171 filed Feb. 6, 1995 by Krzysik et al. The tissues had a length of 12.7 cm., a width of 16 cm., and overlapped the absorbent assembly by less than 1 cm.

Both waist regions of the absorbent article had a length of about 12.7 cm. and a width of 22.1 cm. In the waist regions, the bodyside liner was disposed immediately adjacent to and in contact with the treated tissue, and the treated tissue was disposed immediately adjacent to and in contact with the moisture barrier. The treated tissue was present in about 72 percent of the area of each waist region.

Example N1 (Comparative Example)

An absorbent article was produced comprising a liquid impermeable moisture barrier, a liquid permeable bodyside liner, and an absorbent assembly disposed between the moisture barrier and the bodyside liner. A full length treated tissue was disposed beneath the bodyside liner. These components were bonded together using a construction adhesive. The moisture barrier and the bodyside liner were formed of the same materials and had the same sizes as those in Example A, and the absorbent assembly was formed of the same materials and was the same size as the absorbent assembly in Example C.

The treated tissue was formed of the same treated tissue as in Example M1. The full length treated tissue was rectangular with a length of 69 cm. and a width of 16 cm.

Both waist regions of the absorbent article had a length of about 12.7 cm. and a width of 22.1 cm. In the waist regions, the bodyside liner was disposed immediately adjacent to and in contact with the treated tissue, and the treated tissue was disposed immediately adjacent to and in contact with the moisture barrier. The treated tissue was present in about 72 percent of the area of each waist region.

Example O (Comparative Example)

An absorbent article was produced comprising a liquid impermeable moisture barrier, a liquid permeable bodyside liner, and an absorbent assembly disposed between the moisture barrier and the bodyside liner. Two, two-ply treated tissues were disposed in the waist regions. These components were bonded together using a construction adhesive. The moisture barrier and the bodyside liner were formed of the same materials and had the same sizes as those in Example A, and the absorbent assembly was formed of the same materials and was the same size as the absorbent assembly in Example C.

Other than being 2 plies, the treated tissues were formed of the same treated tissue material as in Example M1. The treated tissues had a length of 12.7 cm., a width of 16 cm., and overlapped the absorbent assembly by less than 1 cm.

Both waist regions of the absorbent article had a length of about 12.7 cm. and a width of 22.1 cm. In the waist regions, the bodyside liner was disposed immediately adjacent to and in contact with the treated tissue, and the treated tissue was disposed immediately adjacent to and in contact with the treated tissue. The moisture control layer was present in about 72 percent of the area of each waist region.

Example P (Comparative Example)

An absorbent article was produced that was exactly the same construction as Example B.

Example Q (Comparative Example)

Another disposable undergarment sold by The Procter & Gamble Company under the trademark ATTENDS® was examined. The product was the same as Example K.

Example W

An absorbent article was produced comprising a liquid impermeable moisture barrier, a liquid permeable bodyside liner, and an absorbent assembly disposed between the moisture barrier and the bodyside liner. The absorbent article also included a tissue layer completely disposed within each waist region. These components were bonded together using a construction adhesive. The moisture barrier and the bodyside liner were formed of the same materials and had the same sizes as those in Example A, and the absorbent assembly was formed of the same materials and was the same size as the absorbent assembly in Example C.

Each tissue comprised a single layer of 22 gsm tissue having a length of 10 cm. and a width of 16 cm. Each tissue was fully contained within its respective waist region and spaced from the absorbent assembly by a gap of about 2.5 cm.

Both waist regions of the absorbent article had a length of about 12.9 cm. and a width of 22.1 cm. In the waist regions, the bodyside liner was disposed immediately adjacent to and in contact with the tissue layer, and the tissue layer was disposed immediately adjacent to and in contact with the moisture barrier. The tissue layer was present in about 57 percent of the area of each waist region.

Example X

An absorbent article was produced comprising a liquid impermeable moisture barrier, a liquid permeable bodyside liner, and an absorbent assembly disposed between the moisture barrier and the bodyside liner. The absorbent article also included a tissue layer completely disposed within each waist region. These components were bonded together using a construction adhesive. The moisture barrier and the bodyside liner were formed of the same materials and had the same sizes as those in Example A, and the absorbent assembly was formed of the same materials and was the same size as the absorbent assembly in Example C.

Each tissue comprised a single layer of 22 gsm tissue having a length of 7.6 cm. and a width of 16 cm. Each tissue was fully contained within its respective waist region and spaced from the absorbent assembly by a gap of about 5.1 cm.

Both waist regions of the absorbent article had a length of about 12.9 cm. and a width of 22.1 cm. In the waist regions, the bodyside liner was disposed immediately adjacent to and in contact with the tissue layer, and the tissue layer was disposed immediately adjacent to and in contact with the moisture barrier. The tissue layer was present in about 43 percent of the area of each waist region.

Example Y

An absorbent article was produced comprising a liquid impermeable moisture barrier, a liquid permeable bodyside liner, and an absorbent assembly disposed between the moisture barrier and the bodyside liner. The absorbent article also included a tissue layer completely disposed within each waist region. These components were bonded together using a construction adhesive. The moisture barrier and the bodyside liner were formed of the same materials and had the same sizes as those in Example A, and the absorbent assembly was formed of the same materials and was the same size as the absorbent assembly in Example C.

Each tissue comprised a single layer of 22 gsm tissue having a length of 11.5 cm. and a width of 16 cm. Each tissue was fully contained within its respective waist region and spaced from the absorbent assembly by a gap of about 1.3 cm.

Both waist regions of the absorbent article had a length of about 12.9 cm. and a width of 22.1 cm. In the waist regions, the bodyside liner was disposed immediately adjacent to and in contact with the tissue layer, and the tissue layer was disposed immediately adjacent to and in contact with the moisture barrier. The tissue layer was present in about 66 percent of the area of each waist region.

Example Z

An absorbent article was produced comprising a liquid impermeable moisture barrier, a liquid permeable bodyside liner, and both an absorbent assembly and a moisture control layer disposed between the moisture barrier and the bodyside liner. These components were bonded together using a construction adhesive. The moisture barrier and the bodyside liner were formed of the same materials and had the same sizes as those in Example A, and the absorbent assembly was formed of the same materials and was the same size as the absorbent assembly in Example C.

The moisture control layer comprised two webs of material that were disposed between the bodyside liner and the moisture barrier in the waist regions. The moisture control layer comprised webs formed of a 120 gsm latex bonded web of rayon fibers. The webs were both rectangular with a length of 16 cm. and a width of 12.7 cm., with the webs positioned so as to overlap the absorbent assembly by less than about 1 cm.

Both waist regions of the absorbent article had a length of about 12.9 cm. and a width of 22.1 cm. In the waist regions, the bodyside liner was disposed immediately adjacent to and in contact with the moisture control layer, and the moisture control layer was disposed immediately adjacent to and in contact with the moisture barrier. The moisture control layer was present in about 72 percent of the area of each waist region.

The absorbent articles of the above Examples were each tested to determine the extent that liquid from the absorbent assembly was transported into the waist regions or end seals of the product. The absorbent articles were tested according to the following procedure. The absorbent article was laid flat on a horizontal surface. If the absorbent article included leg elastics, the leg elastics were removed using a scissors without cutting into the absorbent assembly. A 500 milliliter solution of 0.9 percent saline solution having either a blue or green color was prepared. The color chosen was that thought to be most visible in the absorbent article given the color of the components. The saline solution was poured onto the center of the bodyside surface of the article at a moderate rate to allow liquid to enter the absorbent article without loss, for example, in about 1 minute. The product was allowed to lay flat for between six and seven hours without handling and adding weight onto the product. The distribution of the blue or green saline solution was then visually noted. The results of this test are set forth in Table 1 below:

TABLE 1

Whole Product Bench Test Results

| Example No. | Observed condition of product |
| --- | --- |
| Comparative A | Substantially no liquid was present in the waist regions. |
| Comparative B | Liquid was present in a majority of both waist regions. |
| C | Substantially no liquid was present in the waist regions. |
| D | Substantially no liquid was present in the waist regions. |

TABLE 1-continued

Whole Product Bench Test Results

| Example No. | Observed condition of product |
|---|---|
| E | Substantially no liquid was present in the waist regions. |
| F | Substantially no liquid was present in the waist regions. |
| G | Substantially no liquid was present in the waist regions. |
| H | Substantially no liquid was present in the waist regions. |
| I | Substantially no liquid was present in the waist regions. |
| J | Substantially no liquid was present in the waist regions. |
| Comparative K | Liquid was present in a majority of one waist region and about a quarter of the second waist region. |
| Comparative M1 | Liquid was present in a majority of both waist regions. |
| Comparative N | Substantially no liquid was present in the waist regions. |
| Comparative N1 | Liquid was present in a majority of both waist regions. |
| Comparative O | Liquid was present in a majority of both waist regions. |
| Comparative P | Liquid was present in a majority of both waist regions. |
| Comparative Q | Liquid was present in a majority of both waist regions. |
| W | Substantially no liquid was present in the waist regions. |
| X | Substantially no liquid was present in the waist regions. |
| Y | Substantially no liquid was present in the waist regions. |
| Z | Substantially no liquid was present in the waist regions. |

The moisture control layers from Examples C through J and W through Z were tested to determine their total water absorption capacity and liquid wicking value. Where several Examples employed the same moisture control material, the tests were conducted only once. The results of this test are set forth in Table 2 below:

TABLE 2

Wicking Test Results

| Example No. | Wicking Rate (cm./30 min) | Total Capacity (grams) | Total Capacity (gram per gram) |
|---|---|---|---|
| C | 0 | 1.47 | 3.98 |
| D | Same as C | Same as C | Same as C |
| E | 0 | 5.96 | 11.62 |
| F | Same as E | Same as E | Same as E |
| G | 0 | 4.91 | 10.98 |
| H | Same as G | Same as G | Same as G |
| I | 0 | 10.58 | 10.71 |
| J | Same as I | Same as I | Same as I |
| W | 5 | 1.15 | 4.94 |
| X | Same as W | Same as W | Same as W |
| Y | Same as W | Same as W | Same as W |
| Z | 0 | 10.50 | 9.24 |

For purposes of comparison, the materials that were placed in the waist or end seal regions of comparative Examples B, K, M1, N, N1, O, P and Q were also tested for both their total water absorption capacity and liquid wicking value. The wicking tests for Examples M1 and N were based on two samples, and the total capacity test for Example N was based on two samples. The results of this test are set forth in Table 3 below:

TABLE 3

Wicking Test Results-Comparative Examples

| Example No. | Wicking Rate (cm./30 min) | Total Capacity (grams) | Total Capacity (gram per gram) |
|---|---|---|---|
| Comparative B | 5 | 1.15 | 4.94 |
| Comparative K | N/A | N/A | N/A |
| Comparative M1 | 10 | 3.24 | 6.49 |
| Comparative N | 0 | 3.98 | 9.95 |
| Comparative N1 | Same as M1 | Same as M1 | Same as M1 |
| Comparative O | Same as M1 | Same as M1 | Same as M1 |
| Comparative P | Same as B | Same as B | Same as B |
| Comparative Q | N/A | N/A | N/A |

Finally, several products were worn during normal daytime activities to determine the dryness and comfort level provided when the absorbent assembly was not insulted with liquid. Each product was worn for about 4 hours. The undergarment of Example A was found to be generally sticky, sweaty and hot, while the undergarments of Examples B and C were generally found to be comfortable.

The foregoing detailed description has been for the purpose of illustration. Thus, a number of modifications and changes may be made without departing from the spirit and scope of the present invention. For instance, alternative or optional features described as part of one embodiment can be used to yield another embodiment. Additionally, two named components could represent portions of the same structure. Therefore, the invention should not be limited by the specific embodiments described, but only by the claims.

We claim:

1. An absorbent article having a longitudinal axis, the absorbent article comprising:

a moisture barrier comprising a liquid impermeable material, the moisture barrier having a first end edge and a second end edge longitudinally separated from the first end edge;

an absorbent assembly having opposite longitudinal ends, the absorbent assembly disposed on the moisture barrier between the first and second end edges;

a liquid permeable bodyside liner bonded to the moisture barrier with the absorbent assembly disposed therebetween, the moisture barrier and the bodyside liner extending beyond the longitudinal ends of the absorbent assembly and defining first and second waist regions between the longitudinal ends and the respective first and second end edges, the first and second waist regions each having a width dimension and having a length dimension parallel to the longitudinal axis and greater than about 10 centimeters; and first and second moisture control layers each having a liquid wicking rate of less than about 3 centimeters per 30 minutes and a total water capacity of at least about 0.5 gram, the first moisture control layer disposed in the first waist region, the second moisture control layer disposed in the second waist region and longitudinally spaced from the first moisture control layer, the first and second moisture control layers present in about 25 to 100 percent of the area of the respective first and second waist regions.

2. The absorbent article of claim 1, wherein the moisture control layers have a total water capacity of from about 1 to about 15 grams.

3. The absorbent article of claim 2, wherein the absorbent assembly has a saturated retention capacity greater than about 100 grams.

4. The absorbent article of claim 1, wherein the moisture control layers are substantially inelastic.

5. The absorbent article of claim 1, wherein the moisture control layers are disposed exclusively in the first and second waist regions and are longitudinally separated from the absorbent assembly by at least about 1 centimeter.

6. The absorbent article of claim 1, wherein:
the first waist region has an area more than about 280 square centimeters; and
a portion of the first moisture control layer is disposed exclusively in the first waist region and has an area of more than about 130 square centimeters.

7. The absorbent article of claim 1, wherein the moisture control layers are disposed immediately adjacent to and in contact with the bodyside liner, and the bodyside liner is disposed immediately adjacent to and in contact with the moisture barrier.

8. The absorbent article of claim 1, wherein the bodyside liner is disposed immediately adjacent to and in contact with the moisture control layers, and the moisture control layers are disposed immediately adjacent to and in contact with the moisture barrier.

9. The absorbent article of claim 1, wherein the bodyside liner is a single layer fabric.

10. The absorbent article of claim 1, wherein the moisture barrier comprises a substantially vapor impermeable material.

11. An absorbent article having a longitudinal axis, the absorbent article comprising:
a moisture barrier comprising a liquid impermeable material, the moisture barrier having a first end edge and a second end edge longitudinally separated from the first end edge;
an absorbent assembly having opposite longitudinal ends and a saturated retention capacity greater than about 100 grams, the absorbent assembly disposed on the moisture barrier between the first and second end edges;
a liquid permeable bodyside liner bonded to the moisture barrier with the absorbent assembly disposed therebetween, the moisture barrier and the bodyside liner extending beyond the longitudinal ends of the absorbent assembly and defining first and second waist regions between the longitudinal ends and the respective first and second end edges, the first and second waist regions each having a width dimension and having a length dimension parallel to the longitudinal axis and greater than about 10 centimeters; and
first and second substantially inelastic moisture control layers each having a liquid wicking rate of less than about 3 centimeters per 30 minutes and a total water capacity of from about 1 to about 15 grams, the first moisture control layer disposed exclusively in the first waist region, the second moisture control layer disposed exclusively in the second waist region and longitudinally spaced from the first moisture control layer, the first and second moisture control layers present in about 25 to 100 percent of the area of the respective first and second waist regions.

12. A method of making an absorbent article having a longitudinal axis, comprising the steps of:
providing a moisture barrier comprising a liquid impermeable material, the moisture barrier having a first end edge and an opposite second end edge longitudinally spaced from the first end edge;
disposing an absorbent assembly on the moisture barrier between the first and second end edges, the absorbent assembly having opposite longitudinal ends;
disposing a liquid permeable bodyside liner on the moisture barrier with the absorbent assembly disposed therebetween, the moisture barrier and the bodyside liner extending beyond the longitudinal ends of the absorbent assembly and defining first and second waist regions between the longitudinal ends and the respective first and second end edges, the first and second waist regions each having a width dimension and having a length dimension parallel to the longitudinal axis and greater than about 10 centimeters;
providing first and second moisture control layers each having a liquid wicking rate of less than about 3 centimeters per 30 minutes and a total water capacity of at least about 0.5 gram;
positioning the first moisture control layer in the first waist region with the moisture control layer present in about 25 to 100 percent of the area of the first waist region;
positioning the second moisture control layer in the second waist region and longitudinally spaced from the first moisture control layer, the second moisture control layer present in about 25 to 100 percent of the area of the second waist region: and bonding the moisture barrier, the bodyside liner and the moisture control layers together.

13. A method of making an absorbent article having a longitudinal axis, comprising the steps of:
providing a first continuous web comprising a liquid impermeable moisture barrier;
disposing a plurality of absorbent assemblies on the first continuous web at spaced locations;
providing a plurality of sheets of a moisture control material, the moisture control material having a total water capacity of from about 1 to about 15 grams;
disposing the sheets of moisture control material on the first continuous web between neighboring absorbent assemblies;
providing a second continuous web comprising a liquid permeable bodyside liner,
bonding the first continuous web, the second continuous web and the sheets of moisture control material together, with the absorbent assemblies disposed between the first and second continuous webs; and
transversely cutting the first continuous web, the second continuous web and the sheets of moisture control material at locations between the neighboring absorbent assemblies to form a plurality of individual composite structures, each composite structure comprising an absorbent assembly disposed between a bodyside liner and a moisture barrier, the moisture barrier and the bodyside liner extending beyond longitudinal ends of the absorbent assembly and defining first and second waist regions between the longitudinal ends and respective first and second end edges of the moisture barrier, the first and second waist regions each having a width dimension and having a length dimension parallel to the longitudinal axis and greater than about 10 centimeters, the cut sheets of moisture control material forming a first moisture control layer disposed in the first waist region and a second moisture control layer disposed in the second waist region and longitudinally spaced from the first moisture control layer, the first and second moisture control layers present in about 25 to 100 percent of the area of the respective first and second waist regions.

* * * * *